Figure 1:
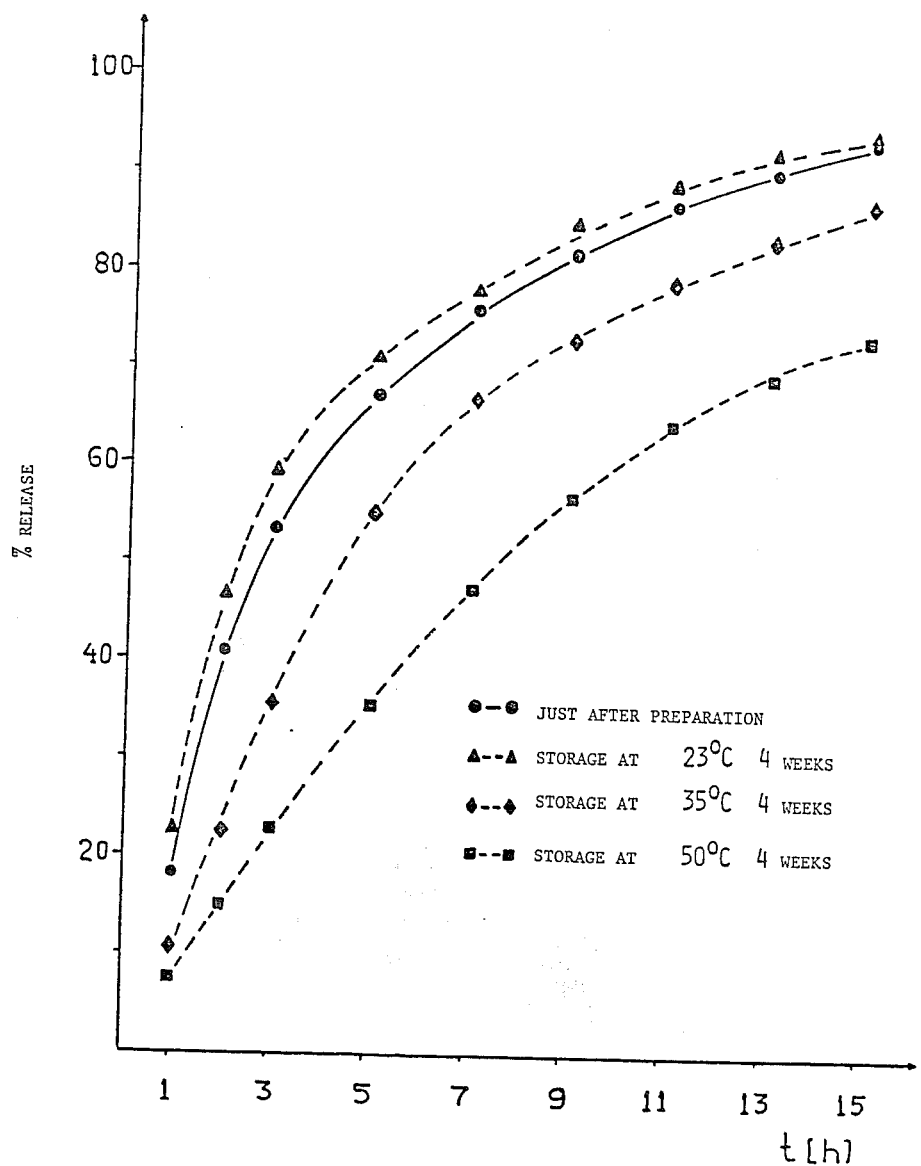

United States Patent [19]

Ventouras

[11] Patent Number: 4,728,513

[45] Date of Patent: Mar. 1, 1988

[54] GRANULAR DELAYED-RELEASE FORM OF PHARMACEUTICALLY ACTIVE SUBSTANCES

[75] Inventor: Kimon Ventouras, Le Lignon, Switzerland

[73] Assignee: Zyma SA, Nyon, Switzerland

[21] Appl. No.: 888,610

[22] Filed: Jul. 23, 1986

[30] Foreign Application Priority Data

Jul. 31, 1985 [GB] United Kingdom ............... 8519310

[51] Int. Cl.$^4$ .................... A61K 33/14; A61K 31/78
[52] U.S. Cl. .................................. 424/461; 424/468; 424/480; 424/495; 424/153; 424/151; 514/81; 514/89; 514/62; 514/100
[58] Field of Search ............... 424/19, 33, 468, 461, 424/480, 495; 514/81, 89, 62, 100

[56] References Cited

U.S. PATENT DOCUMENTS

| | | | |
|---|---|---|---|
| 3,523,906 | 8/1970 | Vrancken et al. | 424/33 |
| 3,712,867 | 1/1973 | Schon et al. | 424/33 |
| 4,083,949 | 4/1978 | Benedikt | 424/19 |
| 4,150,110 | 4/1979 | Yoshida et al. | 424/33 |

FOREIGN PATENT DOCUMENTS

| | | |
|---|---|---|
| 85/03437 | 8/1985 | PCT Int'l Appl. |
| 2087235 | 5/1982 | United Kingdom |
| 0077956 | 4/1983 | United Kingdom |

Primary Examiner—Joseph L. Schofer
Assistant Examiner—Peter F. Kulkosky
Attorney, Agent, or Firm—Michael W. Glynn; Irving M. Fishman

[57] ABSTRACT

A granular delayed-release form of pharmaceutically active substances, which is prepared by coating a granulated or crystalline pharmaceutically active substance, or mixtures thereof, with a coating material mixture consisting essentially of a homogeneous mixture of a poly(H+meth)-acrylic acid-(methyl+ethyl)ester which is insoluble but dispersible in water and an ethyl cellulose which is insoluble but dispersible in water in the weight ratio of 20:1 to 1:5, is presented, which is characterized by the fact that the coated granules are heated for at least 5 minutes at elevated temperatures ranging from between 50° to 120° C.

22 Claims, 11 Drawing Figures

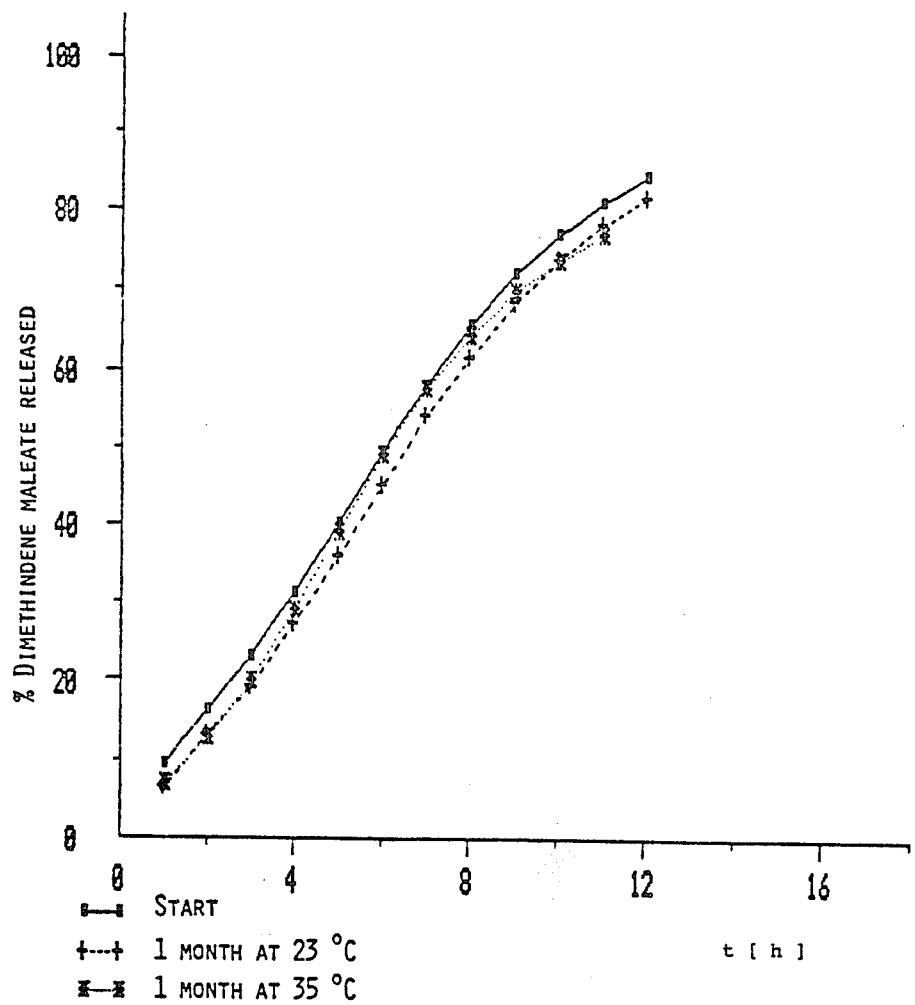

PERCENT RELEASED OF DIMETHINDENE MALEATE
FROM COATED MICRO-PELLETS WITH AND WITHOUT HEAT TREATMENT

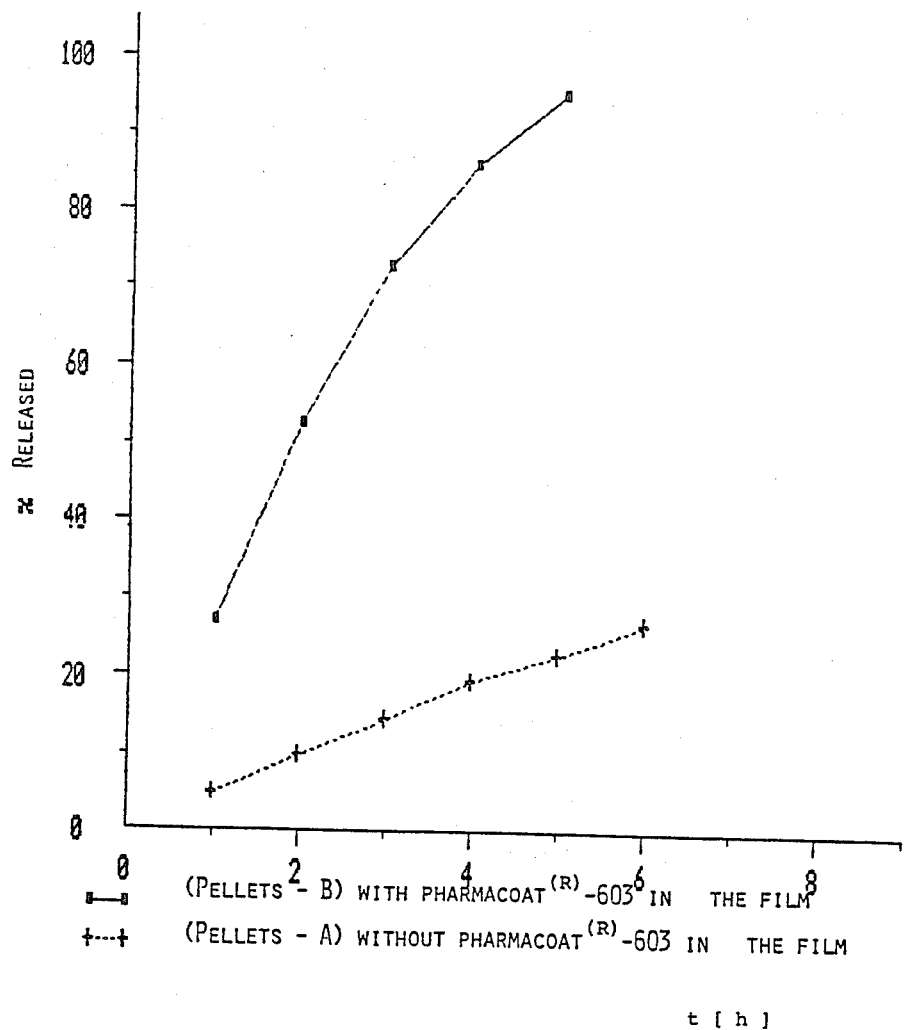

GRANULAR DELAYED-RELEASE FORM OF PHARMACEUTICALLY ACTIVE SUBSTANCES

The invention relates to an improved granular delayed-release form of pharmaceutically active substances.

It is known that a pharmaceutically active substance or mixtures thereof—either in the form of crystals or of granulates—can be coated with coating substances retarding the release of the active substance(s). The delayed release granular forms thus obtained can either be administered directly or be administered after being filled into capsules or after further processing into tablet form. The direct administration of granular delayed-release forms of pharmaceutically active substances is particularly advantageous when a relatively large single dose must be applied, since a tablet or another shaped form, e.g. a capsule, would be too voluminous for oral intake. Furthermore, children and elderly people often have troubles swallowing tablets or other shaped forms.

Granular delayed-release forms of pharmaceutically active substances known hitherto have various disadvantages. There are difficulties in connection with their production: the mode of production is complicated, as for example the use of organic solvents may be necessary, or the auxiliaries used are not ideal for the desired effect namely, the correctly delayed release of active substances. Problems arise also with respect to the external properties of these granules, for example, unsatisfactory free flowability or sensitivity to moisture, disadvantages which become unpleasantly evident either in connection with the direct administration, that is to say with dosing and possibly with the simultaneous intake e.g. of food, or with the filling of the capsules or the manufacture of the tablets.

A granular delayed-release form of pharmaceutical active substances which overcomes these disadvantages is known from the EP-A-52 075, which form contains a granulated or crystalline pharmaceutically active substance coated with coating materials retarding the release of the active substances. These coating materials consist essentially of a homogenous mixture of a polyacrylate which is insoluble but dispersible in water and a cellulose ether which is insoluble but dispersible in water.

It has now suprisingly been found, that a subsequent heating of coated granules similar to those disclosed in EP-A-52 075 improves the properties of the granules in many respects: They are, for example, more storage-stable and the release is evidently further delayed and shifted towards zero order in comparison to the non-heated granules.

Thus, the process according to the invention for the manufacture of a granular delayed-release form of a pharmaceutical active substance, or mixtures thereof, wherein a granulated or crystalline pharmaceutically active substance, or mixtures thereof, is coated with a coating material mixture consisting essentially of a homogeneous mixture of a poly(H+meth)-acrylic acid-(methyl+ethyl) ester which is insoluble but dispersible in water and an ethyl cellulose which is insoluble dispersible in water in the weight ratio of 20:1 to 1:5, is characterised in that the coated granules are heated for at least 5 minutes at elevated temperatures ranging from between 50° to 120° C.

The coated granules are heated e.g. in a fluidised-bed granulator at elevated temperatures ranging preferably from between 50° to 100° C., especially from between 60° to 90° C. and particularly from between 65° and 80° C. The duration of heating is preferably at least 15 minutes and more preferably from at least 15 minutes up to 1,2 or more hours. The duration of heating depends on the temperature employnd: the lower the temperature, the longer the heating period necessary to obtain the desired effect. For the preferred temperature range of 65°-80° C., normally a duration of 15 to 60 minutes, especially 30 to 60 minutes, is sufficient to obtain the desired effect. Of course, one may heat for a much longer time, e.g. 24 or 48 hours at 50° C., if one wants to do so, without deteriorating the granules of the invention significantly.

Suitable active ingredients for the granular delayed-release form of pharmaceutically active substances according to the invention are in particular granular or crystalline substances remaining stable and being insensitive to the elevated temperatures employed. Especially suitable are solid granules or monocrystals within the range of size of 0.05–2 mm (diameter), preferably of 0.1–2 mm, more preferably of 0.3–2 mm, especially of 0.3–1.2 mm and particularly of 0.3–0.5 mm.

All pharmaceutically active substances which can be used for petoral administration and for which a delayed release in the gastro-intestinal tract is desired are essentially suitable, in the form of granules or crystals of an appropriate size, for being processed according to the invention. Preferred are water-soluble substances of this kind. The present invention is particularly advantageous with respect to the use of active substances which, when used at a fairly high concentration, can cause local irritation of the mucous lining of the gastro-intestinal tract, and/or which are administered in large single doses. This applies for example in the case of potassium chloride administered e.g. in the treatment of hypopotassaemia, or in the cane of lithium salts administered e.g. in psychotherapy, or in the case of non-steroidal antinflammatory drugs, e.g. ibuprofen or pirprofen, or in the case of calcium salts e.g. in the therapy of hypocalcomic states or for calcium supplementation, or in the case of sodium fluoride e.g. in the treatment of ostcoporosis, or in the case of pridinol, or salts thereof, e.g. as a muscle relaxant, or in the case of dimethindene, or salts thereof, e.g. as an antihiataminicum, or in the case of methyl-xanthines, e.g. proxyphilline, diprophylline and/or theophylline, e.g. as bronchodilators, or in the case of a mixture of O-β-hydroxyethylated rutins (Venoruton ®) e.g. in the treatment of vanous diseases. All the salts mentioned above must of course be pharmaceutically acceptable so as to be processed according to the invention.

The coating consists on the one hand of particular polyacrylates of the formula

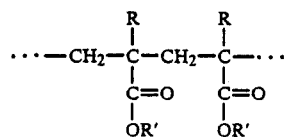

in which R is hydrogen or methyl, and R' is methyl or ethyl.

Substances of this type can be prepared e.g. by emulsion polymerisation.

The homo- or copolymers obtained are in the form of latex particles with a diameter of around or below 1 μm.

A corresponding product being particularly suitable is sold by Röhm Pharma GmbH, Darmstadt (Fed. Rep. of Germany) under the name of Eudragit ®-E30D; this is in the form of an aqueous dispersion, and is an ethyl acrylate/methyl methacrylate 70:30 copolymer having a molecular weight of about 800'000.

On the other hand the coating consists of ethyl cellulose. A particularly suitable product is e.g. that sold by FMC Corporation, Philadelphia (Pennsylvania, USA), under the name of Aquacoat ®-ECD-30, which is in the form of a 30% aqueous polymeric dispersion having a low particle size (latex form) and a narrow particle-size distribution. The above mentioned two coating materials [poly(H+meth)-acrylic acid-(methyl+ethyl) ester and ethyl cellulosel] are e.g. used in the weight ratio of 9:1 to 1:5. Preferred is a weight ratio of 20:1 to 1:1, especially 14:1 to 2:1 and particularly 9:1 to 4:1, e.g. 5:1.

It may be advantageous to blend the coating material mixture according to the invention e.g. with small amounts of antistatic substances, for example 0.5 to 1% of colloidal silicium dioxide, e.g. Aerosil ®, which is marketed by Deguses, Frankfurt (Fed. Rep. of Germany), in order to improve the free flowability of the granules, Preferably, talcum (e.g. 0.5-2%) may be used for this purpose. There can be added to the coating-material mixture other auxiliaries in small amounts, for example dyestuffs.

The release of a pharmaceutically active substance, or mixture thereof, from the granular delayed-release form of the invention can be further influenced, i.e. adjusted to a desired rate, by the addition of water-soluble substances, e.g. sugar, lactose, munnitol, sodium chloride, sorbitol, polyvinylpyrrolidone, polyvinylvinylacetate or polyethylenglycol; and/or swelling substances, e.g. hydroxy-propylcellulose, sodium carboxymethylcellulose, polyvinylalcohol, hydroxyethylcellulose or sodium alginares: and/or water-insoluble substances, e.g. talcum or magnesium stearate; to the coating material mixture (cp. Example 9 and FIG. 5b).

The coating step can be performed in a manner known per se, e.g. in a fluidised-bed spraying apparatus known for this purpose. The coating material mixture is fed in as an aqueous dispersion at room temperature, and spraying is best performed with air at a temperature of 25° to 45° C. It is possible to operate according to either the co-current or the countercurrent principle; the former is however preferred. The individual granules are readily obtained in this manner, without any undesirable agglomeration.

The advantages of the heated granules according to the invention over similar non-heated granules known in the art can be summarized as follows:

(a) The heat-treated granules are far more storage-stable than the non-heated ones. As a result thereof, the dependency of the release curves (% release versus time) on the storage duration and temperature is considerably reduced. Thus the reproducibility of the release curves is much better in case of the heat-treated granules. This can be seen e.g. from a comparison of FIGS. 1 and 1a, or from a comparison of FIGS. 3a and 3b, or from the data given in Tables 2 and 3.

(b) The heat-treated granules show an evidently slower release of the active substance(s) than identical non-heat-treated granules. This is demonstrated e.g. in FIGS. 3c, 4, 5a, 6 and 7, also by the data of Table 1, or by a comparison of FIGS. 1 and 1a.

(c) The release of the active substance(s) from heat-treated granules is shifted towards zero order and is therefore very constant for a long period of time after administration in contract to the release from non-heat-treated granules. This can be seen e.g. from FIG. 3c or from a comparison of FIGS. 1 and 1a.

(d) As the release of active substance(s) generally is slowed down by the heating process of the invention, in case of the heat-treated granules a lower quantity of coating materials can be used to obtain a desired release than in cane of the non-heat-treated granules. Two advantages result therefrom: (1) granules of a certain release behaviour can be prepared more economically (cheaply): (2) it becomes possible to prepare very small—coated—particles, e.g. with 0.1-0.5 mm diameter size, or even down to 0.05-0.1 mm diameter size.

The new granular delayed-release form of a pharmaceutically active substance, or mixtures thereof, obtained by the heating process described above forms another object of the invention. The granules of the invention exhibit a release behaviour completely different from that of the non-heated granules known in the art and thus must be distinct—physically and may be chemically—from the latter. Probably the heating of the invention causes—in ideal case—a fusion or at least a moving together of the spherical latex particles of the coating. In other words, the packing of the spheres becomes more dense, a coalescing of the spheres occurs. This is due to mollification of the spheres and also due to the fact that the tenside and co-tenside molecules located at the surface of the latex spheres in part diffuse into the spheres during the heating process, The tenside and co-tenside molecules mentioned originate from the starting polyacrylate and ethyl cellulose dispersions, e.g. Eudragit ®-E30D and Aquacoat ®-ECD-30. Thus, less hydrophilic tenside/co-tenside molecules can be found on the surface of the latex spheres and moreover in the channels between the spheres after heating. The consequences are that the coating film does not swell as strongly as before heating, that the permeation of the dissolved active substance is smaller and thus the release of the latter is more delayed.

The pharmaceutical active-substance granules produced according to the invention can be applied as such, being then used for individual dosing or for incorporation into liquids (for example suspended in medical syrups) or for incorporation into foodstuffs, or beverages. The commercial preparation would then be packed in customary containers for solids, with or without a dosing device or sachets. Capuules are also suitable for the pre-measured administration of the pharmaceutically active-substance granules prepared according to the present invention.

The pharmaceutically active-substance granules produced according to the invention can also easily be compressed, advantageously together with an agent having good disintegrating and binding properties and with customary auxillaries otherwise used for tabletting. Thus, moulded shapes, for example tablets, or capsular or rod-shapeu compressed products, e.g. as shown in EP-A-52 075. are obtained which allow the dosage of pharmaceutically active substances within a wide range. These formed shapes have the property of rapidly disintegrating into separate granules in the zastrointestinal tract and hence becoming well dispersed. A localised overconcentration of the active substance in the digestive tract is in this way prevented, and a uniform, slowly occuring release of the active substance disperand over a large resorption area is ensured. It has been established by microscopic examination that the individual granules are scarcely damaged as a result of compression, so that on release of the active substance from the granules, the active substance is able to bring into effect its original advantageous properties virtually completely. When a formed or moulded shape has to be produced with two or more active substances, it is possible to prepare separately and dye individually the granules of each pharmaceutically active substance used, a factor which improves identification and which renders the patient aware of the fact that the preparation being taken contains two or more active substances.

Suitable as disintegrating agents having binding properties for the formed shapes obtainable according to the invention are in particular crosslinked polyvinylpolypyrrolidone (PVPP), for example polyplasdone® XL marketed by the GAF Corporation, New York, N.Y. (USA), or Kollidon® CL (BASF, Ludwigahafen/Khein, Fed. Rep. Germany), or sodium carboxymethyl starches, for example Primojel® marketed by W. A. Scholten's Chemicals Fabriken N. V. Foxhol (NL), or Explotab® marketed by E. Mendell Co. Inc., New York (USA).

Auxiliaries customarily used for tabletting, are e.g. binders, lubricants and antisticking agents.

The usual tablet-compressing machines can be used for producing the formed shapes obtainable according to the invention. Since the mechanical strength of the formed shapes produced out of the granules according to the invention is surprisingly good, it is possible to produce all the desired customary forms, for example tablets, capsules or rod-shaped moulded products, with or without breaking grooven. These compressed products can be provided if desired with a protective coat of lacquer known for this purpose.

The following example are intended to illustrate the invention and are not to be construed as being limitation thereon. Temperature are given in degrees Centigrade.

EXAMPLE 1

337.5 g proxyphilline, 337.5 g diprophylline, 225 g theophylline, 45 g Projel®-PA-5 (pregelatinized slightly oxydized potato starch), 146.25 g Avicel®-PH-101 (microcrystalline cellulose) are mixed in a planetary mixer (Erweka) for 10 minutes. This mixture is humidified with a solution of 34 g of glycerine in 100 g of water, The resulting mass is kneaded for about 10 minutes and then extruded through a screen with holes size of 0.8 mm diameter (apparatus Fuji Paudal). The extruded mass is spheronised during 60 seconds with a marumerizer with a speed of 1100 rpm. The obtained microparticles are then dried for 40 minutes at 40° in a fluidised bed (Aeromatic Strea-1). Then 300 g of these microparticles are coated in the same apparatus with a co-current techniques with a dispersion mixture of 214 g Eudragit®-E30D and 36 g Aquacoat®-ECD-30. The spray rate of the coating mixture is 5 g/minute and the inlet air temperature is 40°. At the end a soiution of 15 g Aquacoat in 7 g of water is sprayed on. The pellets obtained are dried for about 30 minutes at 40° and then cooled with air of 22°.

Figure 1A:
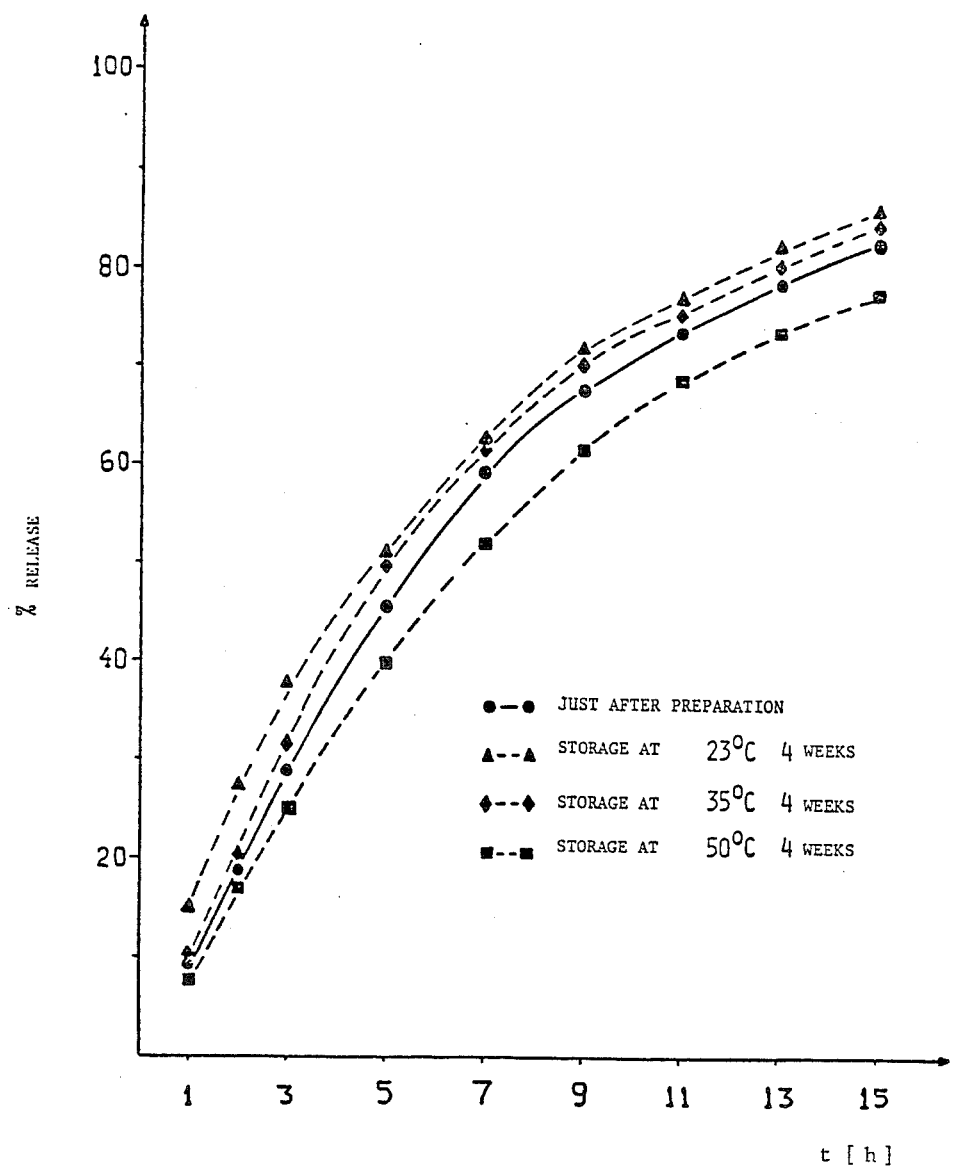

The release rate of 474 mg of these pellets containing 300 mg of the above-mentioned methyl-xanthines is tested in artificial gastric juice according to Pharm. Halv. VI at 37° with the dissolution apparatus no. 2 of USP XX at 50 rpm. The percentages of the three xanthines (total) released just after preparation and after four weeks of storage at 23°, 35° and 50° are shown in FIG. 1.

Another part of the same pellets is treated in a fluidised-bed (Aeromatic Strea-I) for 2 hours at 74° and then cooled with air of 22°. Again the release rate is measured as described above and shown in FIG. 1a.

EXAMPLE 2

(a) Coated micropellets 333 g proxyphilline, 333 g diprophilline, 220 g theophylline, 30 g Projel®-PA-5 end 50 g Avicel®-PH-105 are mixed in a planetary mixer (Erwaka) for 10 minutes. This mixture is humidified with a solution of 10 g of silicone emulsion, 40 g Eudragit®-E30D, 60 g Aquacoat®-ECD-30 and 20 g water. This mass is kneaded for about five minutes and then extruded through a screen with holes size of 0.5 mm diameter (apparatus Fuji Paudal). The extruded mass in spheronized with a marumerizer with a speed of 900 rpm for 30 seconds. The microparticles obtained are dried for about 20 minutes at 50°. 300 g of these microparticles are coated in a fluidised-bed (Aeromatic Strea-1) in a co-current technique with a dispersion mixture of 214 g Eudragit®-E30D and 36 g Aquacoat®-ECD-30. The spray rate of coating mixture is 5 g/minute and the inlet air temperature is 30°, At the end, there is also a spray-on with a solution of 15 g Aquacoat®-ECD-30 in 7 g water. The coated micropellets are then treated in a fluidized bed for 2 hours at 70°.

(b) Tablets prepared from the micropellets described in (a)

The coated micropellets of (a) are compressed into tablets as follows:

46.5 g of the micropellets obtained, 5.3 g Avicel®-PH-101, 31.1 g Elcoma®-G-250 (cellulose powder), 12.6 g polyplasdone®-XL, 3.9 g talcum, 0.2 g Aerosil®-200 and 0.4 g magnesium stonrate are mixed in a powder mixer (Turbula). With the help of a hydrolic tablet press (SPECAC) with a punch of 20 mm diameter with bevelled edges this mixture is transformed into tablets of a thickness of 9 mm and a weight of 2803.4 mg.

The hardness of these tablets is about 170 Newton. The disintegration and dispersion in a glass of water at room temperature is below one minute. One of these tablets contains 900 mg of the mixture of methyl-xanthines, the total release of which is tested as described in example 1.

Figure 2:
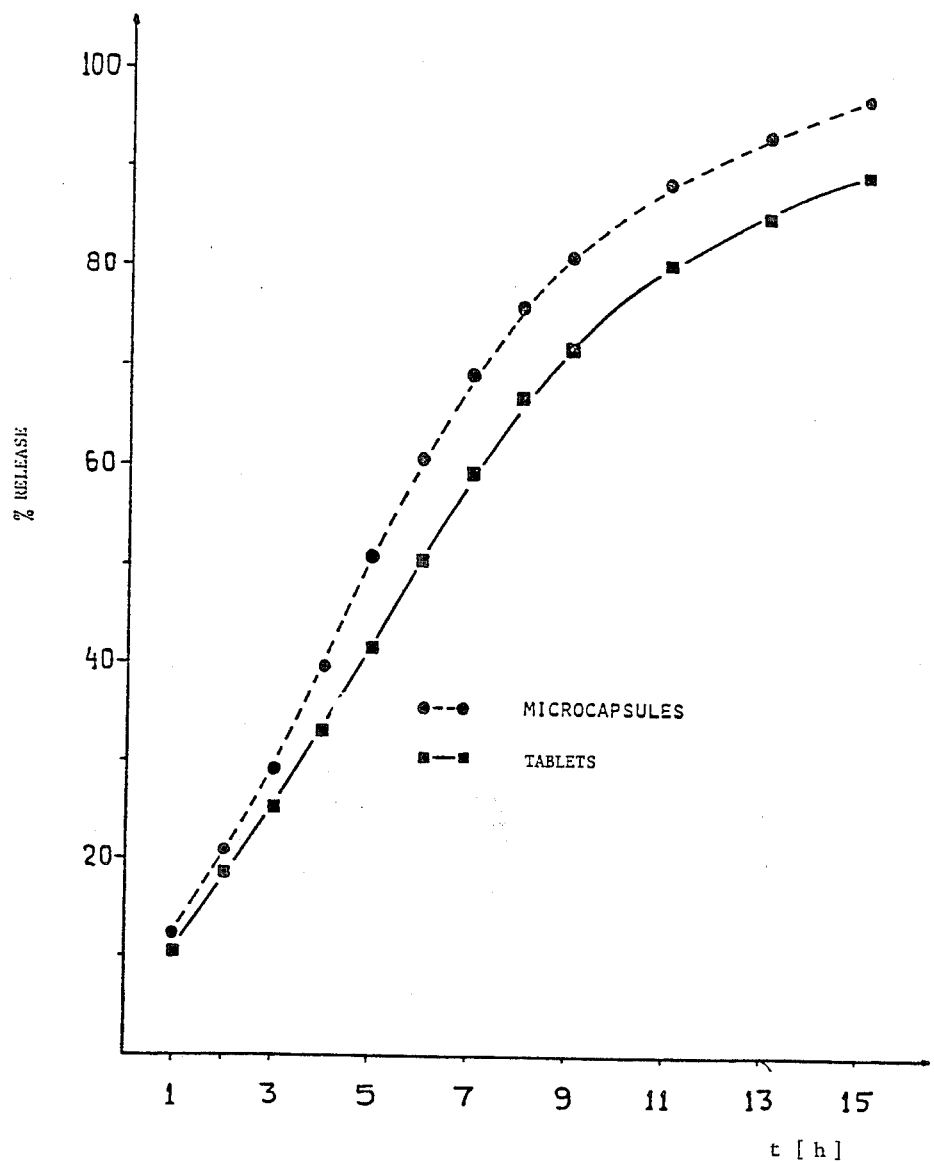

The release profiles of the micropellets and the tablets of this example are shown in FIG. 2.

EXAMPLE 3

Preparation of a mixture containing the micropellets of Example 2(a) which is suitable for the direct administration as a granular delayed-release form e.g. in addition to foodstuffs after dispersion 46.4 g of the micropellets of example 2a are mixed in a powder mixer (Turbula) for 20 minutes with 5.3 g Avicel®-PH-101, 31.1 g Elcema®-0-250, 12.6 g polyplasdone®-XL, 0.2 g Aerosil®-200, 1.8 g banana-aroma in the form of a powder and 17.8 g Primojel®. An amount of 3.231 g of this mixture contains about 900 mg of xanthines in the proportions described above. This mixture can be used e.g. as a suspension in water, beverages or foodstuffs, e.g. jam or apple sauce.

EXAMPLE 4

Composition

| | |
|---|---|
| potassium chloride having a particle size of 0.3–0.8 mm | 750.0 mg |
| Eudragit ®-E30D solid | 157.5 mg |
| Aquacoat ®-ECD-30 | 34.0 mg |
| Aquacoat ®-ECD-30 | 17.5 mg |
| talcum (Pharmacopoe Helvetica) | 15.0 mg |
| | 974.0 mg |

Production

1. Starting material is potassium chloride (KCl).
2. Eudragit ®-E30D and Aquacoat ®-ECD-30 are mixed together with slight stirring.
3. 1. is sprayed with 2. in a fluidized-bed granulator (for example a fluidised-bed granulator Aeromatik AEST 7 or Aeromatik AES 1.30):
   spraying is achieved according to the co-current principle
   the mixture of the two dispersions is stirred during the spraying-operation
   the spraying operation is repeated thereafter solely with Aquacoat ®-ECD-30 (second portion thereof).
4. After the whole amount of the dispersion mixture has been sprayed on, the coated KCl is dried for about 10 minutes in the fluidised-bed dryer as mentioned above.
5. The coated and dried KCl granules are then mixed with talcum for 10 minutes.
6. Thereafter the coated granules are heated in a fluidised-bed at 70° up to 1 hour as given in Table 1 below.

TABLE 1

Release properties for potassium chloride [modified Vanderkamp disintegration tester (USP)] in water at 37° (% of released potassium chloride in dependency of the duration of heating and of the time after starting the in vitro disintegration test)

| determination after X hours | duration of heating at 70° (min) | | | | | |
|---|---|---|---|---|---|---|
| | 0 | 5 | 10 | 20 | 30 | 60 |
| 1 | 19.5 | 15.0 | 9.0 | 6.0 | 5.5 | 4.0 |
| 2 | 45.5 | 39.5 | 33.0 | 30.0 | 28.0 | 27.0 |
| 6 | 97.0 | 94.5 | 90.5 | 87.0 | 87.0 | 87.5 |

The results in Table 1 show that the release of KCl is reduced evidently when heating for a period longer than 15 minutes is performed.

EXAMPLE 5

Two pellets batches of 0.4–1.0 mm diameter size of dimethindene maleate are prepared according to the following formula and process.

A mixture of 165 g powdered dimethindene maleate, 1674 g lactose powder, 620 g Avicel ®-PH-105, 145 g Projet ®-PA-5 and 1322 g glutamic acid powder is prepared in a Dioann mixer P-25 for 5 minutes. This mixture is humidified with a solution of 207 g of silicone emulsion and 992 g of water. The wetted mass is kneaded for about 3 minute in the Dionna mixer and then extruded through a screen with holes size of 0.7 mm diameter (apparatus Fuji Paudel ECDS-60). The extruded mass is spheronised in a spheroniser (Sphoromat-400) with a speed of 610 rpm for 60 seconds. The microparticles obtained are then dried for about 20 minutes at 50°. 6 kg of these microparticles are coated in a fluidised-bed (Aeromatic S-2, 10 bar) in a co-current technique with a dispersion mixture consisting of 135 g Pharmacoat ®-603, 81 g talcum, 54 g titanium dioxide and 2190 g of water. The spray rate of the coating suspension is 40 g/minute and the inlet air temperature is 45°. At the end, 5635 g of these coated micropellets, size 0.4–1.0 mm diameter, are coated further in the same apparatus with a mixture of 2002g Eudragit ®-E30D and 408 g Aquacoat ®-ECD-30. The spray rate of the coating mixture is 40 g/minute and the inlet air temperature is 40°. At the end, there is also a spray-on with a solution of 556 g Aquacoat ®-ECD-30 in 280 ml of water. The coated microparticles are dried for 10 minutes at 40°. Then a small quantity of these pellets is taken out of the fluidised-bed and stored for the stability test. The main quantity of these pellets is treated in the fluidised-bed for 2 hours at 70° and stored for the stability test.

Figure 3A:
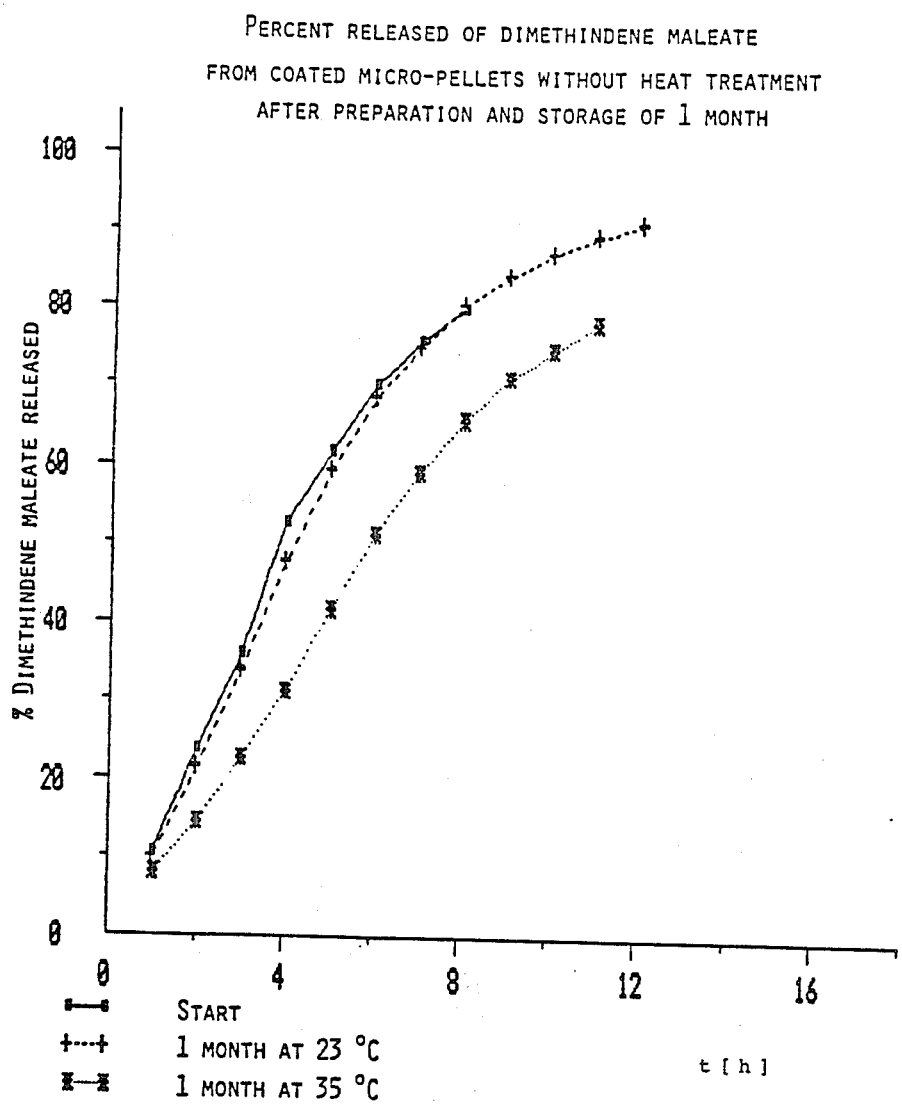
Figure 3:
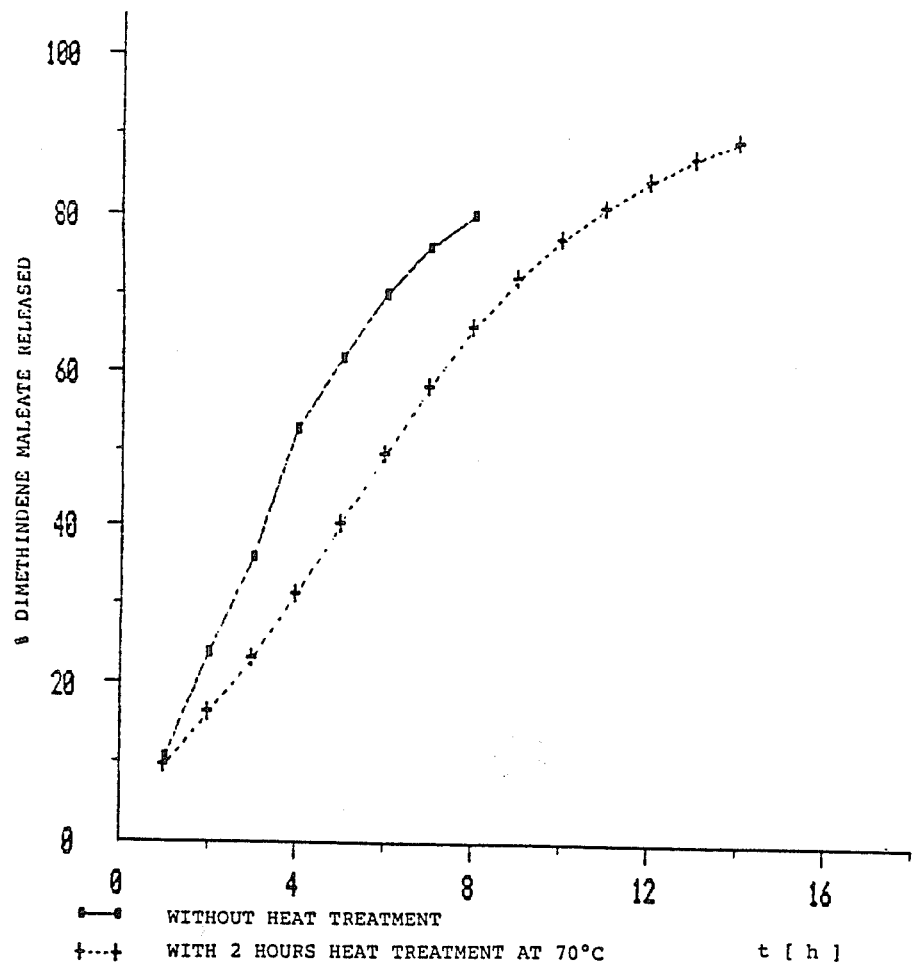

The results of release "in vitro" of dimethindene maleate from these pellets directly after preparation and after a month of storage without heat treatment are presented in FIG. 3a.

The results of release "in vitro" of dimethindene maleate from these pellets directly after preparation and after a month of storage with heat treatment, are presented in FIG. 3b.

From these results (FIGS. 3a, 3b) the favourable influence of the heat treatment on the release rate-"in vitro"-stability of dimethinden maleate from the coated micropellate is evident. In FIG. 3c the "Start" curves of FIGS. 3a and 3b (obtained directly after preparation without and with heat treatment) are plotted together for easier comparison. FIG. 3c clearly demonstrates, that the release of the active substance from the coated micropellets is evidently plowed down and shifted towards zero order due to the heating process of the invention.

EXAMPLE 6

Approximately 2 kg pellets, size 0.315–0.8 mm, of dimethindene maleate are prepared as follows:

A mixture of 80 g powdered dimethindene maleate, 300 g Avicul ®-PH-105, 60 g of Prejel ®-PA-S, 900 g of lactose powder and 640 g of glutamic acid powder is prepared in an Erweka SW-1 mixer for 5 minutes. This mixture is humidified with a solution of 20 g of silicone emulsion in 500 g water. This mass is kneaded for about 5 minutes in the Erweka mixer, and then extruded through a screen with holes size of 0.5 mm diameter (apparatus Fuji Paudal EXKS-1). The extruded mass is spheronised with a marumeriser Q-230 with a spend of 1100 rpm for 60 seconds. The micropellets obtained are dried for about 15 minutes at 40° in an Aeromalic Strea-7 fluidised-bed. 400 g of these micropellets are coated in a fluidised-bed (Aeromatic Strea-1) in a co-current technique with a dispersion mixture consisting of 12 g Pharmacoat ®-603, 7.2 g talcum and 4.8 g titanium dioxide in 144 g of water. The spray rate of the coating mixture is 5 g/minute and the inlet air temperature in 35°. After drying, 413 g of these coated pellets are coated again in the same apparatus with a mixture of 223 g of Eudragit ®-E30D and 44 g of Aquacoat ®-ECD-30. The spray rate of the coating mixture is 7 g/minute and the inlet air temperature is 35°. At the end, there is also a spray-on with a solution of 40 g Aquacoat ®-ECD-30 in 20 g water, The coated micropellets are then treated in the fluidised bed for 2 hours at 70°.

The percentage of dimethindene maleate released directly after preparation and after six months of storage at 23°, 35° and 50° are presented in Table 2:

TABLE 2

Percentage of dimethindene maleate released directly after preparation and after storage of up to six months at 23° C. and 35° C.

| Storage Conditions | | Time | Percentage of dimethindene maleate released at | | | |
|---|---|---|---|---|---|---|
| °C. | R.H. | [months] | 2 h | 4 h | 8 h | 12 h |
| 23° | 50% | start | 18.9 | 32.2 | 70.1 | 93.2 |
| | | 1.5 | 16.8 | 30.1 | 69.6 | 93.2 |
| | | 3.0 | 20.1 | 33.6 | 73.6 | 94.8 |
| | | 6.0 | 18.2 | 32.5 | 73.1 | 93.6 |
| 35° | 30% | 1.5 | 17.9 | 30.0 | 68.2 | 92.7 |
| | | 3.0 | 19.7 | 34.1 | 74.0 | 94.4 |
| | | 6.0 | 20.6 | 37.9 | 78.4 | 95.2 |

R.H. = relative humidity perature is 40°. At the end, a solution of 100 g Aquacoat®-ECD=30 in 50 g water is sprayed on.

The coated particles obtained are treated in a fluidised bed (Aeromatic Strea-1) for 2 hours at 70° and then cooled with air of 32°. In order to obtain a gastro-resistant (enteric coated) product, 2120 g of these coated pellets are coated further with a suspension mixture of 942 g Eudragit®=L30D, 85 g propylene glycol and 141 g talcum in 1093 g water in a fluidised-bed (Aeromatic Strea-1) in a co-current technique. The spray rate of the coating suspension is 7 to 10 g/minute and the inlet air temperature is 40°. At the end, a suspension of 123 g Aquacoat®=ECD-3D, 12.5 g Pharmacoat(R)-603, 25 g talcum, and 123 g water is sprayed on. These pellets are further encapsulated in gelatine capsules size No. 2 with a Zanasi LZ-64 pellets filling equipment and stored for stability.

The precentages of sodium fluoride released "in vitro" directly after preparation and after storage at 23° and 35° for 3 months are presented in Table 3.

TABLE 3

Percentages of sodium fluoride released "in vitro" directly after preparation and after storage of 3 months at 23° C. and 35° C.

| Storage Conditions | | | 2 h SGF pH = 1.2 | 2 h SGF + 1 h SIF pH = 6.8 | 2 h SGF + 2 h SIF pH = 6.8 | 2 h SGF + 3 h SIF pH = 6.8 | 2 h SGF + 4 h SIF pH = 6.8 |
|---|---|---|---|---|---|---|---|
| T [°C.] | R.H. | Time | | | | | |
| | | starting values | 2.4 | 27 | 50 | 70 | 89 |
| 23° | 50% | 3 months | 3.1 | 33 | 60 | 82 | 95 |
| 35° | 30% | 3 months | 2.2 | 28 | 53 | 74 | 87 |

R.H. = relative humidity
SGF = simulated gastric fluid
SIF = simulated intestinal fluid

EXAMPLE 7

Micropellets of dimethindene maleate are prepared and coated with the same composition and quantity of suspension of Pharmacoat®-603 as described in Example 5, but the further coating with the mixture of Eudragit®-E30D : Aquacoat®-ECD-30 is performed in a proportion of 14:1 (2250 g : 161 g) instead of approximately 5:1 as described in Example 5.

Figure 4:
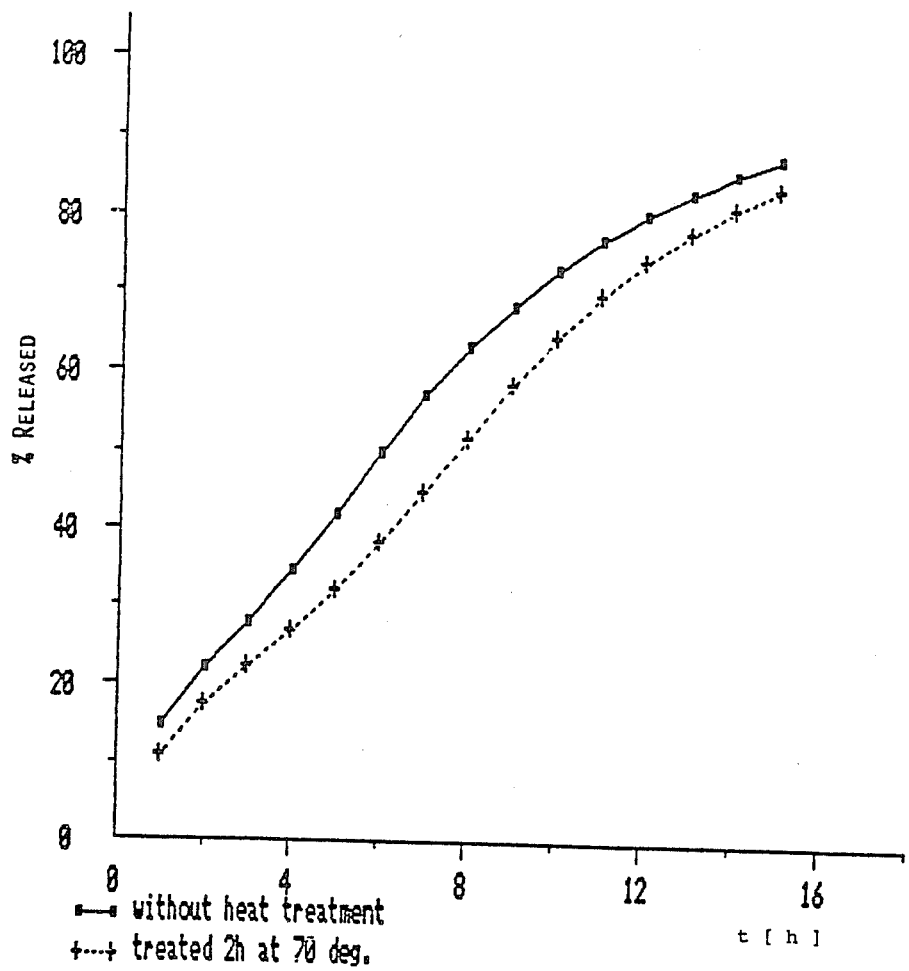

The influence of the heat treatment on the release of dimethindene maleate "in vitro" from these coated micro-pellets is presented in FIG. 4.

EXAMPLE 8

Approximately 8 kg of pellets, size 0.5–1.2 mm, of sodium fluoride are prepared as follows:

A mixture of 3200 g powdered sodium fluoride, 3120 g lactose powder, 1200 g Avicel®-PH-105 and 400 g of Prejel®-PA-5 is prepared in a Diosna P-25 mixer for 5 minutes. This mixture is humidified with a solution of 80 g silicone emulsion and 1987 g water. This mass is kneaded for about 3 minutes in the Diosna, and then extruded through a screen with holes size of 1.0 mm diameter (apparatus Fuji Paudal ECDS-60). The extruded mass is then spheronised in the Diosna mixer for 1 minute. The microparticles obtained are dried for about 20 minutes in an Aeromatic Strea-7 fluidised-bed, and the particles between 0.5–1.2 mm are collected by sieving in an apparatus Engelaman model "various 400/800". 2 kg of these pellets are coated in a fluidised-bed (Aeromatic Strea-1) in a co-current technique with a dispersion mixture of 267 g Aquacoat®-ECD-30 and 267 g of Eudragit®-E30D, The spray rate of the coating suspension is 5 to 7 g/minute and the inlet air tem-

EXAMPLE 9

Pellets (500 g) of the same composition as described in example 8 are prepared, and one portion of these pellets is coated with a dispersion mixture of 111.5 g Eudragit®-E30D and 22.9 g Aquacoat®-ECD-30 in a fluidised-bed (Aeromatic Stea-1) in a co-current technique. The spray rate of the coating mixture is 5 g/minute and the inlet air temperature is 40°. At the end, a solution of 25 g Aquacoat®-ECD-30 in 12.5 g water is sprayed on. These coated pellets are treated for 2 hours at 70° and then cooled with air of 22° (Pellets A).

Another portion of the pellets of example 8 is coated with a solution dispersion of 111.5 g Eudragit®-E30D, 22.9 g Aquacoat®-ECD-30 and 40.1 g of a solution w/w of 20% Pharmacoat®-603 in water. There is also a spray-on with 25 g Aquacoat®-ECD-30 in 12.5 g water. At the end, the coated micro-pellets are treated with heat (70°) for 1,2 (Pellets B) and 4 hours respectively.

Figure 5A:
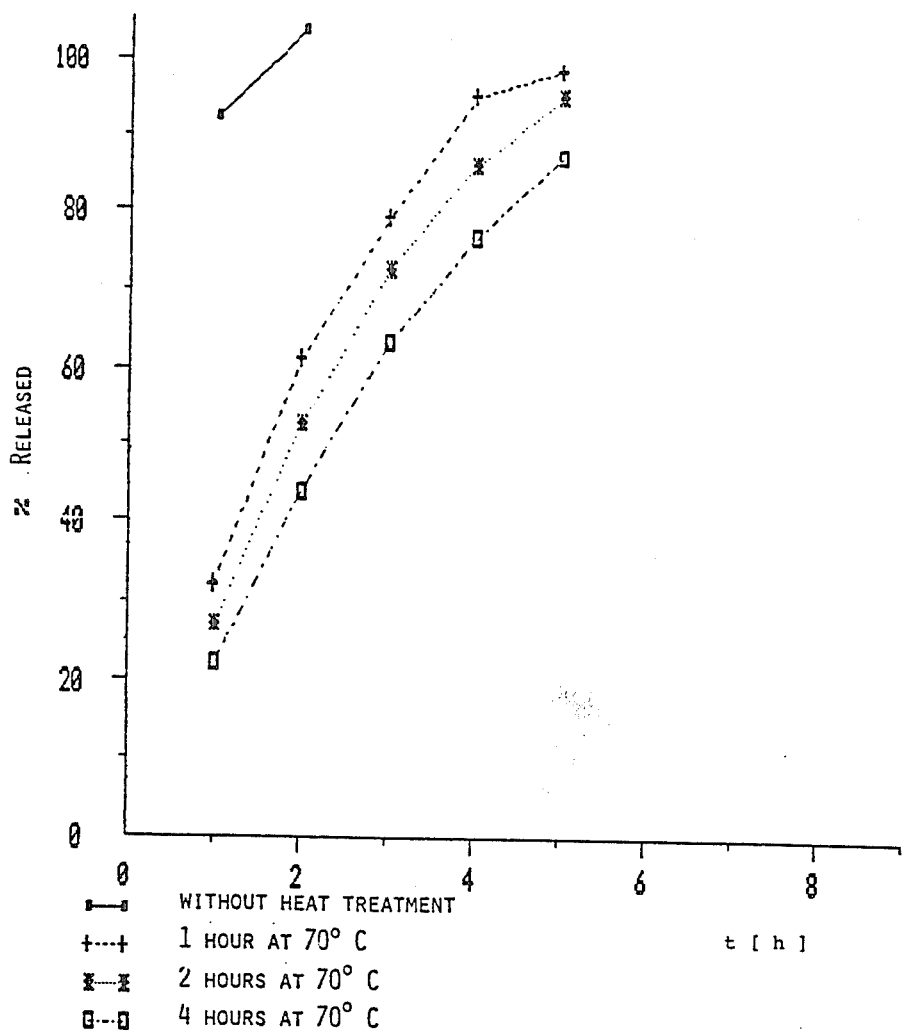
Figure 6:
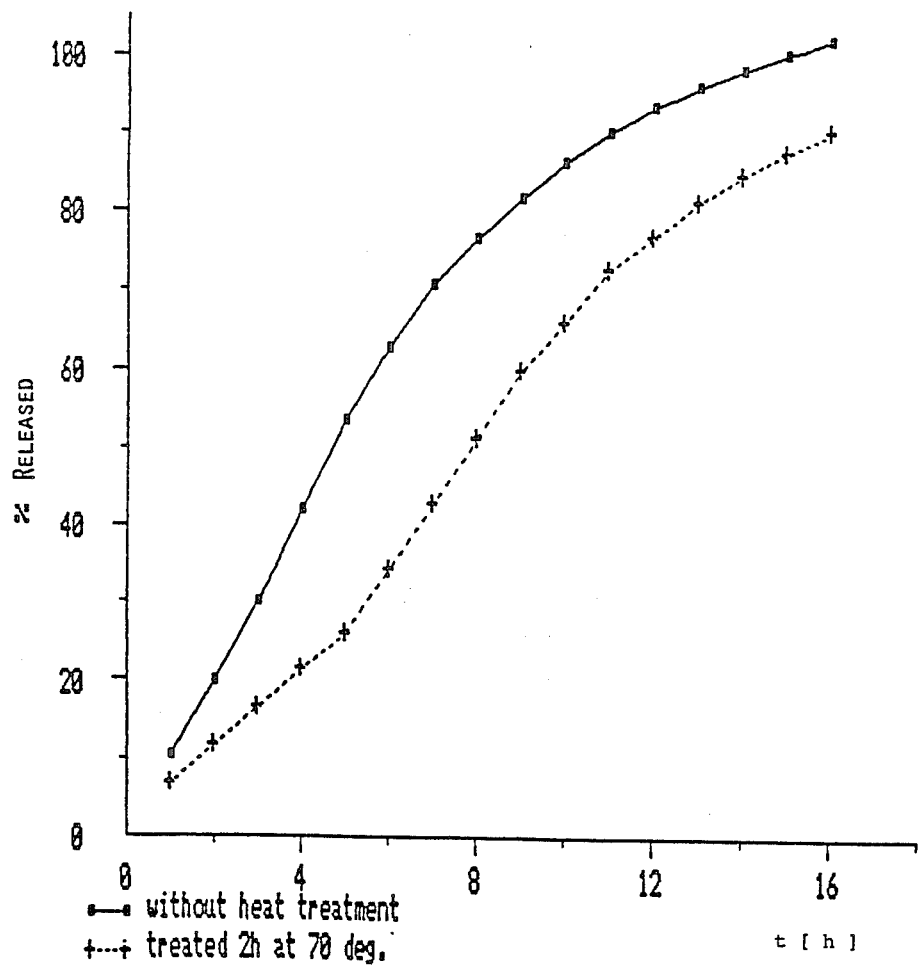

The release rate "in vitro" of sodium fluoride is controlled by the time of heat treatment as can be seen from FIG. 5a.

In FIG. 5b the release behaviour of Pellets A and B is compared. By addition of a small amount of low-substituted hydroxypropylcellulose (e.g. Pharmacoat®-603) the release rate of sodium fluoride is considerably increased.

This is a good example for adjusting the release of a given pharmaceutically active substance (here: sodium fluoride) to a desired rate by the addition of auxiliaries, e.g. water-soluble or swellable or water-insoluble substances, to the coating material mixture. It is important to note, however, that the heat treatment of the coating is essential to get any reproducible delayed release whatsoever.

EXAMPLE 10

Approximately 1.5 kg pellets, size 0.4–1.0 mm, of 1,1-diphenyl-3-(N-piperidino)-1-propanol (pridinol) methanesulfonate are prepared as follows:

A mixture of 60 g powdered 1,1-diphenyl-3-(N-piperidino)-1-propanol methanesulfonate, 225 g Avicel®-PH-105, 607.5 g lactose powder, 52.5 g Frejel®-PA-5 and 480 g of glutamic acid powder is prepared in an Erweka SW-1 mixer during 5 minutes. This mixture is humidified with a solution of 75 g silicone emulsion in 360 g water. This mass is kneaded for about 3 minutes in this mixer and then extruded through a screen with holes size of 0.7 mm diameter (apparatus Fuji Pandal EXKS-1). The extruded mass is apheronised with a marumerizer Q-230 with a speed of 1100 rpm for 60 seconds. The microparticles obtained are dried for about 50 minutes at 50°, 400 g of this micropellets sized 0.4–1.0 mm are coated in a fluidised-bed (Aeromatic Strea-1) in a co-current technique with a dispersion mixture of 144 g Eudragit®-E30D and 29 g Aquacoat®-ECD-30. The spray rate of the coating mixture is 5 g/minute and the inlet air temperature is 40°. At the end, there is also a spray-on with a solution of 40 g Aquacoat®-ECD-30 in 20 g water. The coated particles obtained are dried for about 10 minutes at 40° and then cooled with air of 22°. The main portion of the coated particles obtained is treated further in a fluidised-bed (Aeromatic Strea-1) for 2 hours at 70° and then cooled with air of 22°.

The release rate "in vitro" of these two preparations—one without and the other with heat treatment—from 421 mg coated micropellets containing 15 mg of the above-mentioned active ingredient is tested. The dissolution medium is artificial gastric fluid of pH=1.2 at 37° with the dissolution apparatus No. 2 paddle of USP XX at 50 rpm. The percentage of released 1,1-diphenyl-3-(N-piperidino)-1-propanol methanesulfonate from these coated micropellets, with and without heat treatment, is presented in FIG. 6.

EXAMPLE 11

Microgranules of O-β-hydroxyethylated rutins (Venoruton®) are prepared by wet granulation in a fluidised-bed (Aeromatic S-2, 10 bar). Approximately 8 kg of granules are obtained by wet granulation of 6 kg of O-β-hydroxyethylated rutins and 1.116 kg of Prejel®-PA-5 with a solution of 0.753 kg of O-β-hydroxyethylated rutins in 2.8 kg of water in a fluidised-bed with the counter-current technique. The spray rate of the solution is 40 g/minute, the inlet air temperature is 40° and the inlet air flow is 280 m³/hour. At the end, these granules are dried in the fluidised-bed.

Microgranules of 0.2–0.5 mm are collected by sieving, and 400 g of thene particles are coated in a fluidised-bed (Aeromatic Strea-1) in a co-current technique with a dispersion mixture of 228 g Eudragit®-E30D and 39 g Aquacoat®-ECD-30. The spray rate of coating is 5 g/minute and the inlet air temperature is 40°. At the end, there is also a spray-on with a solution of 40 g Aquacoat®-ECD-30 in 20 g water. The coated microparticles are then dried for 10 minutes at 40° and a small quantity of this material is taken out of the fluidised-bed for release control "in vitro".

The main quantity of these coated microparticles is then treated in the fluidised-bed for 2 hours at 70° and then cooled with air of 22°.

Figure 7:
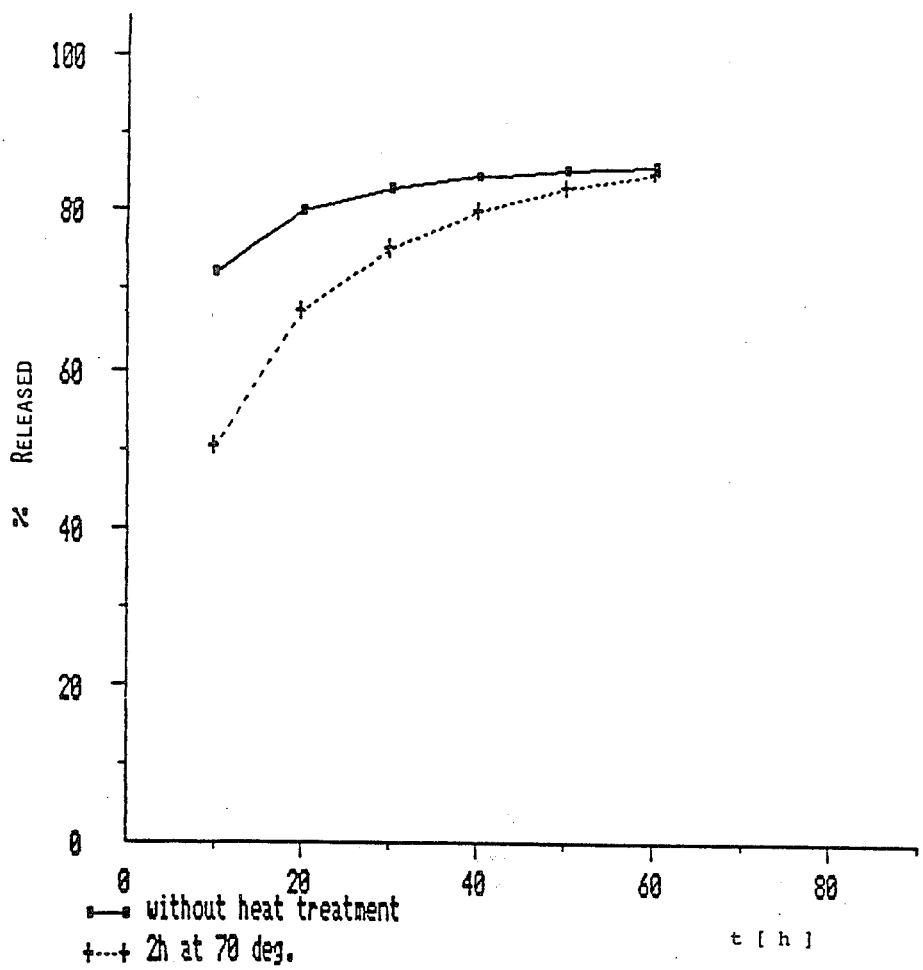

The percentage of released O-β-hydroxyethylated rutins (Venoruton®) from these coated microparticles with and without heat treatment is presented in FIG. 7.

What is claimed is:

1. A process for the manufacture of a granular delayod-release form of a pharmaceutically active substance, or mixtures thereof, wherein a granulated or crystalline pharmaceutically active substance, or mixtures thereof, is coated with a coating material mixture consisting essentially of a homogeneous mixture of a poly(H+meth)-acrylic acid-(methyl+ethyl) eater which is insoluble but dispersible in water and ethyl cellulose which is insoluble but dispersible in water in the weight ratio of 20:1 to 1:5, characterised in that the dry coated granules are then heated for at least 5 minutes at elevated temperature ranging from between 50° to 120° C. whereby the instant heat treated coated granules have improved storage stability, slower release of active substance, and release rate kinetics closer to zero order kinetics than identical granules not so heat treated.

2. Process according to claim 1, characterised in that the coated granules are heated for at least 15 minutes at elevated temperatures ranging from between 60° to 90° C.

3. Process according to claim 1, characterised in that the coated granules are heated for at least 30 minutes at elevated temperatures ranging from between 65° to 80° C.

4. Process according to claim 1, characterised in that the weight ratio of the coating materials poly(H+meth)-acrylic acid ester and ethyl cellulose is 20:1 to 1:1.

5. Process according to claim 1, characterised in that the weight ratio of the coating materials poly(H+meth)-acrylic acid ester and ethyl cellulose is 14:1 to 2:1.

6. Process according to claim 1, characterised in that the weight ratio of the coating materials poly(H+meth)-acrylic acid ester and ethyl cellulose is 9:1 to 4:1.

7. Process according to claim 1 characterised in that the coating material mixture in addition is blended with at least one antistatic substance.

8. Process according to claim 7, characterised in that the antistatic substance is talcum.

9. Process according to claim 1, characterised in that the coating material mixture in addition is blended with at least one auxiliary, which is able to adjust the release of the pharmaceutically active substance(a) used to a desired rate.

10. Process according to claim 9, characterised in that the auxiliary is low-substituted hydroxypropylcellulose.

11. Process according to claim 1, characterised in that the granulated or crystalline pharmaceutically active substance(s) is (are) in the range of size of 0.05-2 mm diameter.

12. Process according to claim 1, characterised in that the granulated or crystalline pharmaceutically active substance(s) is (are) in the range of size of 0.3-1.2 mm diameter.

13. A granular delayed-release form of a pharmaceutically active substance, or mixtures thereof, which is prepared by coating a granulated or crystalline pharmaceutically active substance, or mixtures thereof, with a coating material mixture consisting essentially of a homogeneous mixture of a poly(H+meth)-acrylic acid-(methyl+ethyl) ester which is insoluble but dispersible in water and an ethyl cellulose which is insoluble but dispersible in water in the weight ratio of 20:1 to 1:5, characterised in that the coated granules are heated for at least 5 minutes at elevated temperatures ranging from between 50° to 120° C. whereby the instant heat treated coated granules have improved storage stability, slower release of active substance, and release rate kinetics closer to zero order kinetics than identical granules not so heat treated.

14. A granular delayed-release form of pharmaceutically active substances according to claim 13, characterised in that the active substance is potassium chloride.

15. A granular delayed-release form of pharmaceutically active substance according to claim 13, characterised in that the active substance is a lithium salt.

16. A granular delayed-release form of pharmaceutically active substance according to claim 13, characterised in that the active substance is a non-steroidal antiinflammatory drug.

17. A granular delayed-release form of pharmaceutically active substances according to claim 13, characterised in that the active substance is calcium salt.

18. A granular delayed-release form of pharmaceutically active substances according to claim 13, characterised in that the active substance(s) is (are) proxyphilline and/or diprophylline and/or theophylline.

19. A granular delayed-release form of pharmaceutically active substances according to claim 13, characterised in that the active substance is dimethindene or a pharmaceutically acceptable salt thereof.

20. A granular delayed-release form of pharmaceutically active substance according to claim 13, characterised in that the active substance is sodium fluoride.

21. A granular delayed-release form of pharmaceutically active substances according to claim 13, characterised in that the active substance is pridinol or a pharmaceutically acceptable salt thereof.

22. A granular delayed-release form of pharmaceutically active substances according to claim 13, characterised in that the active substance is a mixture of O-$\beta$-hydroxyethylated rutine.

* * * * *